United States Patent [19]

Fujioka et al.

[11] Patent Number: 5,496,559

[45] Date of Patent: Mar. 5, 1996

[54] POROUS SOLID FORMULATIONS CONTAINING PROTEINACEOUS PHYSIOLOGICALLY ACTIVE SUBSTANCES

[75] Inventors: Keiji Fujioka, Amagasaki; Shigeji Sato, Ibaraki; Yoshihiro Takada, Suita, all of Japan

[73] Assignee: Sumitomo Pharmaceuticals Company, Limited, Osaka, Japan

[21] Appl. No.: 122,430

[22] PCT Filed: Apr. 6, 1992

[86] PCT No.: PCT/JP92/00420

§ 371 Date: Sep. 30, 1993

§ 102(e) Date: Sep. 30, 1993

[87] PCT Pub. No.: WO92/17209

PCT Pub. Date: Oct. 15, 1992

[30] Foreign Application Priority Data

Apr. 8, 1991  [JP]  Japan ........................... 3-074990
Apr. 8, 1991  [JP]  Japan ........................... 3-074991

[51] Int. Cl.$^6$ ........................... A61F 13/02; A61K 47/42
[52] U.S. Cl. ........................... 424/435; 514/773; 514/774; 514/801; 514/953
[58] Field of Search ........................... 424/435; 514/773, 514/774, 801, 953

[56] References Cited

U.S. PATENT DOCUMENTS 4,371,516  2/1983  Gregory et al. ........................... 424/426
4,774,091  9/1988  Yamahira et al. ........................... 424/426
4,950,483  8/1990  Ksander et al. ........................... 424/423

FOREIGN PATENT DOCUMENTS

| 0107941 | 9/1984 | European Pat. Off. |
| 0177342 | 9/1986 | European Pat. Off. |
| 0230647 | 8/1987 | European Pat. Off. |
| 0326151 | 2/1989 | European Pat. Off. |
| 0412554 | 2/1991 | European Pat. Off. |
| 97918 | 5/1985 | Japan . |
| 230729 | 9/1987 | Japan . |
| 198635 | 8/1988 | Japan . |
| 710 | 2/1990 | Japan . |
| 2040292 | 8/1980 | United Kingdom . |
| 8803411 | 5/1988 | WIPO . |
| 9000060 | 1/1990 | WIPO . |

OTHER PUBLICATIONS

Koech, Davy et al., Mol. Biother., vol. 2, 91–95 (1990) The Lancet, 1530–1531 (1987).

*Primary Examiner*—Garlos A. Azpuru
*Attorney, Agent, or Firm*—Birch, Stewart, Kolasch & Birch

[57] ABSTRACT

A solid formulation for buccal or oral administration which contains a proteinaceous physiologically active substance as an active ingredient, as well as collagen and a water-soluble additive, said formulation being characterized by being porous and having a good disintegration property, and a preparation thereof are provided.

8 Claims, 2 Drawing Sheets

POROUS SOLID FORMULATIONS CONTAINING PROTEINACEOUS PHYSIOLOGICALLY ACTIVE SUBSTANCES

FIELD OF THE INVENTION

The present invention relates to a solid pharmaceutical formulation for buccal or oral administration which contains a proteinaceous physiologically active substance as an active ingredient, as well as collagen and a water-soluble additive, said formulation being characterized by being porous and having a good disintegration property, and to a preparation thereof.

THE PRIOR ART

Development of biotechnology, in particular, genetic recombination and cell culture technology has provided and will be providing substantial amount of proteinaceous physiologically active substances such as cytokines and proteinaceous hormones, for the purpose of the treatment and diagnosis in medical and animal industries.

Such proteinaceous physiologically active substances are usually administered via injection, because they have, in general, poor absorption in digestive tracts.

There is a report which demonstrates that buccal administration of a little amount (2 IU/kg/day) of interferon, proteinaceous physiologically active substance, to patients suffering from a disease caused by human immunodeficiency virus type 1 (HIV-1), which is called AIDS, resulted in an improvement in its symptom (Davy K. Koech et al., Mol. Blother. Vol.2, 91–95 (1990)). WO88/03411 describes a method of contacting an interferon to the buccal cavity and the pharyngeal mucosa.

Also, a sustained release formulation which contains interferon and collagen is described in the Japanese Patent Publication (kokai) No. 97918/1985.

However, any stable solid formulations have not yet been known, which can be administered in a form for a buccal or oral route, and which can release proteinaceous physiologically active substances in an amount and over a time necessary for treating the diseases.

DESCRIPTION OF THE PRESENT INVENTION

The inventors of the present invention have completed the invention by making efforts to find the above-noted ideal formulation.

Specifically, the present invention relates to a stable solid pharmaceutical formulation which can be administered in the form suitable for a buccal or oral route, and which can release the proteinaceous physiologically active substances in an amount and over a time necessary for treating the disease, as well as a preparation thereof. More specifically, the present invention relates to a solid pharmaceutical formulation for buccal and oral administrations, which contains a proteinaceous physiologically active substance as an active ingredient, as well as collagen and a water-soluble additive, said formulation being characterized by being porous and having a good disintegration property, and to a preparation thereof.

In one embodiment, the present invention relates to a pharmaceutical formulation for treating AIDS, or for preventing the progress of AIDS, when it contains interferon as a proteinaceous physiologically active substance.

DESCRIPTION OF THE PREFERRED EMBODIMENTS FOR CONDUCTING THE PRESENT INVENTION

Figure 1:
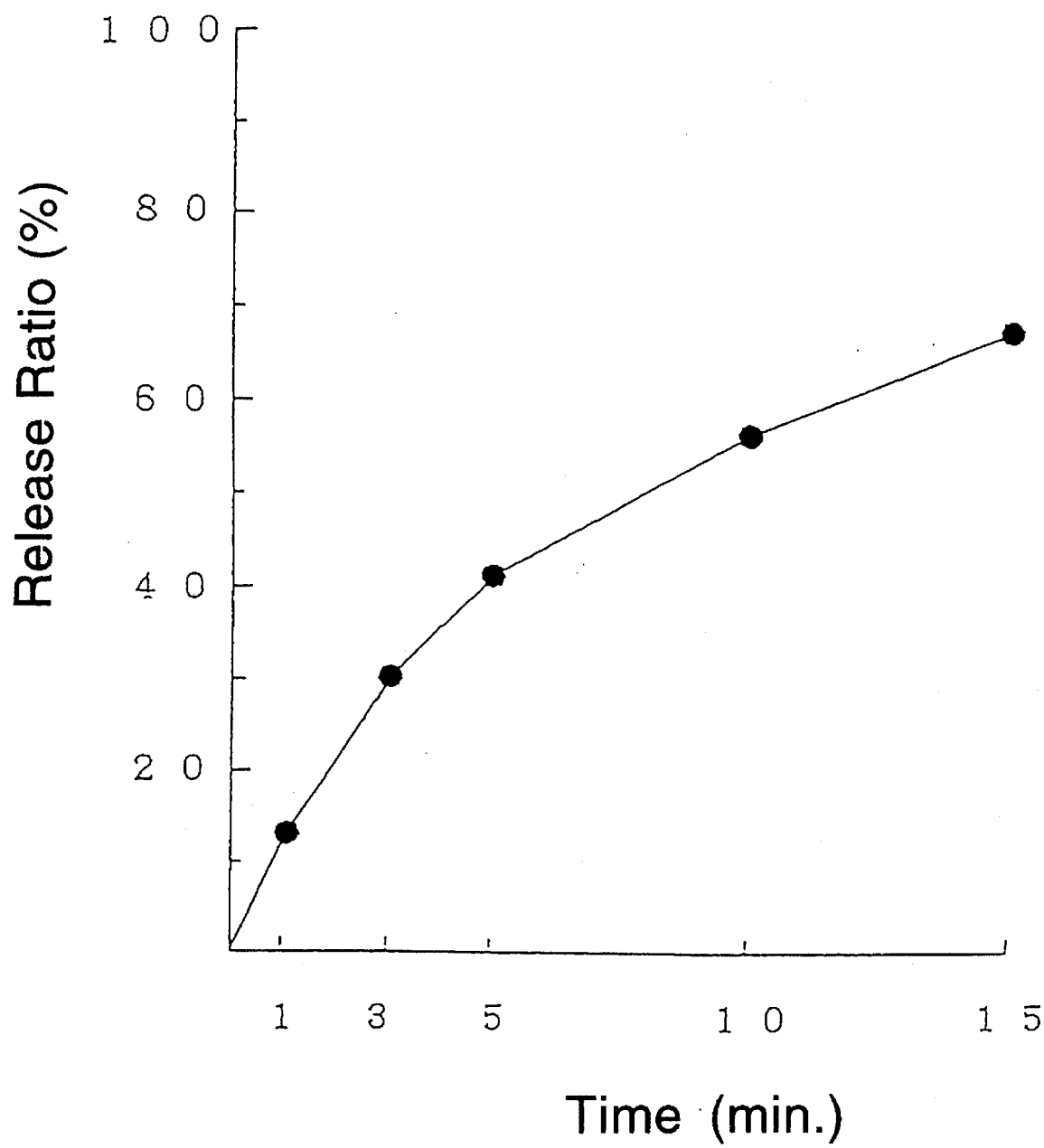
FIG. 1 shows a time-course of a release of interferon from the spongy formulation of the present invention (Example 1).

As shown above, the present invention relates to a solid pharmaceutical formulation for buccal and oral administrations, which contains a proteinaceous physiologically active substance as an active ingredient, as well as collagen and a water-soluble additive, said formulation being characterized by being porous and having a good disintegration property, and to a preparation thereof.

Collagen

"Collagen" which can be used in the invention includes, for example, atelocollagen which is derived from a natural resource, and which is free of a telopeptide which is an antigenic portion of collagen; chemically modified atelocollagen; naturally-occurring collagen, and so on. The collagen which has been chemically derived from the atelocollagen includes, for example, a succinylated collagen, a methylated collagen, and so on. The naturally-occurring collagen includes, for example, a collagen from a skin of bovine, a chorda of bovine, a bowel of porcine and sheep, a human placenta, and so on.

Alternatively, the collagen which is used in the solid formulation of the present invention may be commercially available products. The commercially available products of the collagen usually contain a buffer such as phosphate buffer, citrate buffer, acetate buffer, a stabilizer, and so on. The solid formulation of the invention can contain such buffer or stabilizer.

Water-soluble Additive

"Water-soluble additive" which is used in the solid formulation of the invention may be a water-soluble pharmaceutical additive which is usually used, and includes, for example, proteins, glycoproteins, amino acids, polyamino acids, peptides, saccharides, water-soluble polysaccharides, or a combination thereof. Proteins include, for example, gelatin, albumin, and so on. Glycoproteins include, for example, globulin, and so on. Amino acids include, for example, aspartic acid, arginine, glycine, leucine, and so on. Polyamino acids and peptides include, for example, polyalanine, polyglycine, sodium polygultamate, sodium polyaspartate, polylysine, polyleucine, and so on. Saccharides, polysaccharides, and water-soluble polysaccharides include, for example, fructose, sucrose, lactose, dextran, cyciodextran, mannitol, sorbitol, and so on.

Proteinaceous Physiologically Active Substances

"Proteinaceous physiologically active substances" include, for example, simple proteins, conjugated proteins, derived proteins. In particular, such substances include, for example, a cytokine having activity for modulating immunity, an endocrine-related substance, a proteinaceous hormone, a growth factor, a nutrition factor, an enzyme, and so on, and, more particularly, include interferon, interleukin, colony stimulating factor, macrophage activating factor, and so on. Interferons include interferon-α, interferon-β, interferon-γ, and so on. Interleukins include interleukin-1, interleukin-2, and so on. Colony stimulating factors include multipotency colony stimulating factor (multi-CSF), granulocyte-monocyte macrophage colony stimulating factor (GM-CSF), granulocyte colony stimulating factor (G-CSF), monocyte macrophage colony stimulating factor (M-CSF), and so on.

The proteinaceous physiologically active substances which are used in the solid formulation of the present invention can be any substances, regardless of the preparation therefor, and include an extract from organisms, a synthetic product, a substance from a genetic recombination, a substance from a cell culture.

Alternatively, the proteinaceous physiologically active substances which are used in the solid formulation of the present invention may be commercially available products. The commercially available products of the substances usually contain some additives. The solid formulation of the invention can contain such additives. Such additives are human serum albumin, amino acid, sodium chloride, and so on, in the case of an interferon. When the proteinaceous physiologically active substance is colony stimulating factor, such additives are for example a saccharide, a sugar alcohol, polyethylene glycol. In the case of interleukins, such additives are phosphate buffer, human serum albumin, and so on.

Pharmaceutical Additives

The solid formulation can contain a pharmaceutical additive, if necessary. Such "pharmaceutical additives" include any additives which are usually used, and include, for example, a stabilizer, a preservative, a buffer, a sweetener, a flavor, a binder, a suspending agent, a disintegrator, and so on.

A stabilizer includes one which is used for the proteinaceous physiologically active substances, and, in particular, albumin, gelatin, mannitol, trehalose, and so on. A preservative includes, for example, p-hydroxybenzoates, sorbic acid, salicylic acid, and so on. A buffer includes citrate buffer, acetate buffer, phosphate buffer, and so on. A sweetener includes, for example, mannitol, glucose, maltose, starch, lactose, and so on. A flavor includes, for example, aspartic acid, citric acid, lactic acid, and so on. A binder includes, for example, methylcellulose, ethylcellulose, carboxy methyl cellulose, and so on. A suspending agent includes, for example, Tween 20, Tween 80, and so on. A disintegrator includes, for example, glycerol, starch, and so on.

Porous

The term "porous" is used for describing a formulation which has pores or lacunas. The solid formulation of the present invention comprise a porous collagen matrix having low density. In particular, the solid formulation is in the condition in which the collagen matrix therein has continued pores. The shape of the formulation may be film or sponge.

The solid formulation of the present invention can have a density of 0.1 mg/cm$^3$ to 1 g/cm$^3$. Specifically, the density can be 10 mg/cm$^3$ to 500 mg/cm$^3$, more specifically, 20 mg/cm$^3$ to 200 mg/cm$^3$, and most specifically, 40 mg/cm$^3$ to 100 mg/cm3.

The porosity of the solid formulation can be 99% to 23%, for example. Specifically, the porosity can be 99% to 62%, more specifically, 98% to 85%, and most specifically, 97% to 92%.

Disintegration

The term "disintegration" refers to a phenomenon in which the formed solid formulation is dispersing and dissolving.

Disintegration time is determined according to Disintegration Test (JP XII). Specifically, a test device on which glass tubes having 21.5 mm (i.d.)×23.5 mm (o.d.)×77.5 mm (h) are immobilized is placed into a beaker. To the beaker is added water as a solution for test, and the temperature is kept 37° C. The test formulations are added to the glass tubes, and then the supplemental plates are added into the glass tubes and onto the formulations. Then, the test device is mildly moved up and down with an amplitude of 53 mm to 57 mm at 29 to 32 cycles per minutes. The test device has a net at its bottom (meshes: 2.0 mm, diameter of the line: 0.6 mm). The test formulations which are moved up and down are shaken therein. Time to be required to fully disintegrate is termed as disintegration time.

The disintegration time of the solid formulation of the invention may be within 2 hours. Specifically, the time may be a range between 1 minute and 30 minutes, and more specifically, a range between 3 minutes and 20 minutes, and most specifically, a range between 5 minutes and 15 minutes.

Oral and Buccal Administrations

The term "oral administration" in the solid formulation of the invention refers to an administration by which the formulation is disintegrated and/or dissolved in digestive tracts such as esophagus, stomach, and bowel, and the proteinaceous physiologically active substances are released in the digestive tracts so as to contact to the wall of the tracts. The term "buccal administration" refers to an administration by which the formulation is maintained in buccal cavity, and then disintegrated and/or dissolved therein, and the proteinaceous physiologically active substances are released so as to contact to buccal mucosa, pharyngeal mucosa, and so on.

Preparation

The solid formulations of the present invention can be prepared by the following process.

Each of solutions of the proteinaceous physiologically active substances, the collagen, and the water-soluble additive is prepared, and these solutions are combined together and, if necessary, solution of some pharmaceutical additives are added to the combination to give a homogeneous mixture. Alternatively, each component in a defined amount can also be combined to solvent to give a liquid mixture.

The solvent used to prepare a solution of each of materials includes water, and a hydrophilic solvent, and a preferable solvent is water. A hydrophilic solvent include, for example, an alcohol such as methanol, ethanol, etc., a ketone such as acetone, etc., or a mixture comprising water and the just-mentioned organic solvent.

Concentration of collagen in the mixture is usually below 5% by weight, and specifically the concentration is between 0.01 to 3% by weight, more specifically 0.1 to 2% by weight. Most specifically, the concentration is 0.5 to 2% by weight.

Concentration of total excipient comprising collagen, water-soluble additive and if necessary, pharmaceutical additives in the mixture is usually below 50% by weight, and specifically the concentration is between 0.01 to 30% by weight, more specifically 0.1 to 20% by weight. Most specifically, the concentration is 2 to 20% by weight.

The solid formulation can be prepared so that the amount of the proteinaceous physiologically active substances in the dosage unit form is the amount which is required to treat the diseases in question.

In the case that the proteinaceous physiologically active substance is for example an interferon, and that the subjective disease is AIDS, the amount of the interferon in the dosage unit form may be a range between 10 IU to $10^5$ IU, and specifically, 10 to $10^3$ IU, and more specifically, 40 to 400 IU. The dosage unit form can be administered one time to three times per day.

The temperature at which each of the components is combined may be 5° C. to 30° C., and specifically 5° C. to 20° C.

Then, the above solution or the mixture is dried by the drying procedure such as in vacuo drying, in vacuo concentration, atmospheric drying procedure, etc., to form a suitable shape for the treatment. As the in vacuo drying procedure, in vacuo lyophilization, in vacuo drying in liquid procedure, etc. are conducted. In the case of the in vacuo lyophilization procedure, freezing is conducted at temperature between −40° C. to −30° C., and then the drying is conducted at temperature between 10° C. to 30° C. In the case of in vacuo drying in liquid, the drying is conducted at 5° C. to 30° C.

When the in vacuo lyophilization is conducted, the spongy formulation having the collagen matrix of the density of 0.1 mg/cm$^3$ to 500 mg/cm$^3$ is prepared. Further, when the atmospheric drying is conducted, the filmy formulation having the collagen matrix of the density of 300 mg/cm$^3$ to 1000 mg/cm$^3$ is prepared.

The disintegration time of the solid formulation can be modified if desired. For example, such modification may be conducted by changing the content ratio of the water-soluble additive in the formulation. Specifically, the disintegration time can be shortened by increasing the content ratio of the water-soluble additive. The lower density solid formulation of which disintegration time is more shortened, can be prepared by vigorously shaking the solution or the liquid mixture so as to incorporate the air into the solution or the mixture in the course of the preparation of the solution or the liquid mixture in which the individual components are dispersed homogeneously, followed by lyophilizing it.

Further, the formulation having the desired density may be prepared by modifying the concentration of the entire excipients (collagen, the water-soluble additive, and if necessary, the pharmaceutical additive). For example, when the solid formulation of which disintegration time is the range between 5 to 20 minutes is prepared, it is preferred that the concentration of the entire excipients in the homogeneous solution or liquid mixture is brought to 2 to 20% by weight. When the solid formulation of which disintegration time is the range between 30 minutes to 2 hours is prepared, it is preferred that the concentration of the entire excipients in the homogeneous solution or liquid mixture is brought to 30 to 50% by weight. Further, the solid formulation of which density is high, and of which disintegration time is long, can be prepared by compressing the formulation obtained above. Examples of molds for forming the solid formulations include, but are not limited to, stainless steel mold, resin mold, glass mold, etc.

Examples of the shapes of the solid formulations include, but are not limited to, globular, hemi-globular, needle, spindle, buttony, disklike, filmy, tablet, capsule shapes, etc. In the case of the buccal administration, the hemi-globular, disklike, and filmy forms are preferable. In the case of the oral administration, the globular, tablet, and capsule forms are preferable.

Size of the formulation can be selected arbitrarily if it is suitable for the buccal and oral administrations.

For example, in the case of the disklike formulation, the size may be between 2 to 20 mm in diameter, and between 0.1 to 10 mm in thickness. Preferably, the size is 5 to 10 mm in diameter, and 1 to 5 mm in thickness.

When the filmy, needle, or tablet formulation is administered via the buccal cavity, the size of the formulation can be between 2 to 20 mm in length, preferably, 5 to 10 mm in length.

When the disklike formulation is administered via oral route, the size may be between 2 to 15 mm in diameter, and between 0.1 to 10 mm in thickness. Preferably, the size is 5 to 10 mm in diameter, and 1 to 3 mm in thickness.

When the tablet formulation is administered via oral route, the size of the formulation can be between 2 to 20 mm in length, preferably, 5 to 10 mm in length.

Alternatively, a molded sheet is previously made of a vinyl chloride sheet, which is used in PTP packing, and then, a solution or a liquid mixture in which each of the above components is dispersed homogeneously is added to the sheet, and lyophilized. Then, the sheet is packed with an aluminum foil to provide the formulations which are molded and packed into the PTP packing.

A water content in the solid formulation after drying may be below 20% by weight, specifically below 15% by weight, more specifically below 10% by weight. If the proteinaceous physiologically active substance is stable in the form of the hydration, 3 to 10% by weight of water can be incorporated into the solid formulation.

The ratio of a collagen and a water-soluble additive in the solid formulations of the present invention can be 1:9 to 9:1, for example. Specifically, the ratio is 1:9 to 1:1.

Effect of the Present Invention

As stated above, the solid formulations are porous. When the formulations are administered into the buccal cavity, it will disintegrate and/or dissolve to release the proteinaceous physiologically active substances, since a saliva penetrates the formulation through the pores or chinks therein. At the same time, the water-soluble additives dissolve, and the collagen matrix also disintegrates and/or dissolves, to release the proteinaceous physiologically active substances.

The present invention provides the solid formulation which can release a therapeutically-effective amount of the proteinaceous physiologically active substances at a disintegration and/or dissolution rate suitable for the buccal and oral administrations.

The solid formulations of the present invention have good disintegration property. When the solid formulation is administered to the buccal cavity, the formulation disintegrates and/or dissolves in the cavity gradually so as to release the proteinaceous physiologically active substances. In the oral administration, the formulation disintegrates and/or dissolves in digestive tracts such as esophagus, stomach, and bowel, etc., to release the proteinaceous physiologically active substances.

Further, it is possible to control a disintegration time of the solid formulation of the present invention, and to control a release amount and a release rate of the proteinaceous physiologically active substances from the formulation. Specifically, the release amount and the release time of the proteinaceous physiologically active substances can be readily modified to desired ones by changing the composition or the preparation method of the solid formulations.

As would be obvious from the above, it is easy to prepare a homogeneous formulation, because the formulation is prepared by mixing the components in the form of solutions. Accordingly, one feature of the present invention is a constant release of the proteinaceous physiologically active substances, which is particularly suitable for therapeutical use.

When the solid formulation is administered to the buccal cavity, the formulation absorbs water in the cavity, swells, and assumes viscosity, whereby it adheres to the buccal cavity, and remains therein. Thus, the solid formulation of the invention can be readily maintained in the buccal cavity, and, therefore, the proteinaceous physiologically active substances which is released from the formulation can be readily contacted to the mucosa of the cavity and the pharyngeal mucosa for enough time necessary to the treatment. The solid formulation gives no bad feeling and irritation to buccal cavity.

It is possible to make the solid formulations of the present invention in both small and large scale by the process stated above, and additionally, the solid formulations can be provided in association with good homogeneousness, good reproduction, and high yield. The process of the invention does not require special temperature and pressure in the preparation of the solid formulations. Accordingly, the process of the present invention can be applied to a labile, proteinaceous physiologically active substance to prepare a solid formulation containing such substance.

The following examples are provided to further illustrate the formulation of the present invention. Such examples are representative only and should not be construed as limiting the scope of the invention in any respect.

EXAMPLES

EXAMPLE 1

A liquid mixture containing interferon-α was prepared by mixing completely 120 g of 2% solution of atelocollagen in water, 120 g of 4% solution of gelatin in water, 2.4 g of sucrose, and 80,000 IU of interferon-α. Each 0.3 ml portions of the liquid mixture was placed into pockets in PTP molded sheet (SUMILITE® VSS-1202, a pocket: 10 mm in diameter, 0.35 ml in volume), and lyophilized on a vacuum freeze dryer R2L-30KWS type (Kyowa Shinku). After lyophilization, heat-sealing was conducted with an aluminum foil. The tablets were packed with the PTP packing sheet and the sheet was cut into fragments, each containing 10 tablets.

The resultant tablets each contain 100 IU of interferon-α (1,000 IU of interferon-α corresponds to 10 ng).

EXAMPLE 2

A liquid mixture containing interferon-α was prepared by mixing completely 120 g of 2% solution of atelocollagen in water, 120 g of 4% solution of gelatin in water, 2.4 g of sucrose, and 160,000 IU of interferon-α. Each 0.3 ml portions of the liquid mixture was placed into pockets in PTP molded sheet (SUMILITE® VSS-1202, a pocket: 10 mm in diameter, 0.35 ml in volume), and lyophilized on the vacuum freeze dryer R2L-30KWS type (Kyowa Shinku). After the lyophilization, heat-sealing was conducted with an aluminum foil. The tablets were packed with the PTP packing sheet and the sheet was cut into fragments, each containing 10 tablets.

The resultant tablets each contain 200 IU of interferon-α.

EXAMPLE 3

A liquid mixture containing interferon-α was prepared by mixing completely 120 g of 2% solution of atelocollagen in water, 120 g of 4% solution of gelatin in water, 2.4 g of sucrose, and 800,000 IU of interferon-α. Each 0.3 ml portions of the liquid mixture was placed into wells in microwell plate (the volume of the well: 0.35 ml), and then, dried under reduced pressure, to yield the tablets in hemi-globular forms, each of which contains 1000 IU of interferon-α.

EXAMPLE 4

An aqueous solution (120 ml) was prepared, of which 0.3 ml portions contain 1000 IU of interferon-α, 3 mg of atelocollagen, 6 mg of gelatin, 3 mg of human serum albumin, 3 mg of sucrose. Each 0.3 ml portions of the liquid mixture was placed into wells in microwell plate (the volume of the well: 0.35 ml), and then, lyophilized on the vacuum freeze dryer R2L-30KWS type (Kyowa Shinku), to yield the tablets in the form of hemi-globular, each of which contains 1000 IU of interferon-α.

EXAMPLE 5

An aqueous solution (30 ml) was prepared, of which 0.3 ml portions contain 20 IU of erythropoietin, 3 mg of atelocollagen, 6 mg of gelatin, and 3 mg of glucose. The mixture was treated in a procedure similar to that of Example 3 to yield the formulations, each of which contains 20 IU of erythropoietin.

EXAMPLE 6

An aqueous solution (12 ml) was prepared, of which 0.3 ml portions contain 2 µg of epidermal growth factor (EGF), 3 mg of atelocollagen, 6 mg of gelatin, and 3 mg of lactose. Each 0.3 ml portions of the mixture was placed into pockets in PTP molded sheet (SUMILITE® VSS-1202, a pocket: 10 mm in diameter, 0.35 ml in volume), and lyophilized in a procedure similar to that of Example 1 to yield the formulations, each of which contains 2 µg of EGF.

EXAMPLE 7

An aqueous solution (12 ml) was prepared, of which 0.3 ml portions contain 2 µg of epidermal growth factor (EGF), 3 mg of atelocollagen, 6 mg of gelatin, and 3 mg of lactose. The mixture was treated in a procedure similar to that of Example 4 to yield the formulations, each of which contains 2 µg of EGF.

EXAMPLE 8

An aqueous solution (18 ml) was prepared, of which 0.3 ml portions contain 200 µg of GM-CSF, 6 mg of a methylated collagen, 6 mg of dextran (40), 3 mg of human serum albumin, and 3 mg of maltose. The mixture was treated in a procedure similar to that of Example 4 to yield the formulations, each of which contains of 200 µg of GM-CSF.

EXAMPLE 9

An aqueous solution (120 ml) was prepared, of which 0.3 ml portions contain 1 IU of human growth hormone, 6 mg of a succinylated collagen, 3 mg of sodium polyglutamate, 3 mg of glycine, and 3 mg of mannitol. The mixture was treated in a procedure similar to that of Example 4 to yield the formulations, each of which contains of 1 IU of human growth hormone.

EXAMPLE 10

A liquid mixture containing interferon-α was prepared by mixing completely 18 g of 2% solution of atelocollagen in water, 6 g of 10% solution of gelatin in water, 0.36 g of glucose, and 120,000 IU of interferon-α. The mixture was placed into plastic laboratory dish which have 12 cm of diameter, and then, the dishes were left stand for 7 days at room temperature. The dried products were cut into the slices having sizes of 10 mm×10 mm, to yield the formulation in the filmy form, each of which contains about 1,000 IU of interferon-α.

EXAMPLE 11

Thirty g of 2% solution of atelocollagen in water, 8.46 ml of a solution (70.9 mg/ml) of human serum albumin in water, 0.3 g of glucose, and 0.107 ml of a solution of interferon-α in water (2 millions IU/ml) were mixed, and the mixture was lyophilized. After the lyophilized products were swelled by adding a small amount of a distilled water thereto, an additional distilled water was added to the products until the final concentration of the solid reached 29%. The mixture was fully stirred in a mortar to give a homogeneous mixture. The mixture was placed into a 10 ml disposable syringe, and centrifuged at 10,000 G for 60 minutes so that the mixture was degassed. A membrane of Gore-Tex® (porous tetrafluoroethylene) was immobilized on a U-shaped aluminum material. The centrifuged mixture of the solid at 29% concentration obtained above was pushed out from the nozzle having 1.7 mm i.d., to place on the Gore-Tex® membrane linearly. The linear products were carefully placed in a sloping condition into a desiccator where the relative humidity was kept 75%, and dried for 72 hours in a refrigerator, and then further dried for 24 hours in the desiccator containing silica gel.

The resultant dried products was cut into pieces having suitable length, to yield needle pellets having 0.9 mm diameter, each of which contains 1,000 IU of interferon-α.

EXAMPLE 12

The formulations of the present invention have an ability to keep the active component stable. In this example, a stability test was conducted using the formulation of Example 1, which was prepared by applying the present invention to interferon-α.

Three sheets of the PTP packing formulations, which were prepared in Example 1 were kept at 40° C. in a thermostat. Each one sheet of them was removed from the thermostat at 0.5, 1 and 2 months after starting the experiment, and the contents of interferon-α in the formulations were quantified by a method provided below. The content of interferon-α at the beginning of the experiment was quantified and the contents at any later stage representing residual contents were expressed with percentage (%) when the initial content is assumed as 100.

Content Quantification

Three of 10 tablets in one sheet were picked up, and each of them was added to 5 ml of the RIA buffer (PBS buffer containing 0.5% human serum albumin, and 0.01% sodium azide), and the mixtures were kept as they were for 20 hours at room temperature. Then, the mixtures were warmed at 37° C. for 5 minutes, and mixed with shaking to yield homogeneous solutions. The concentrations of interferon-α in the mixtures were determined by RIA, and the content in each one of three tablets was calculated. The resultant three values were averaged to obtain data. RIA was conducted according to the known method, using RIA kit (interferon-α RIA kit) from DAINABOT Co.

The test results are shown in Table 1. From the data, it is suggested that the formulations of the present invention have long term stability.

TABLE 1

| Sample | storage temperature | storage term | a residual content (%) of interferon-α |
|---|---|---|---|
| Example 1 | 40° C. | starting point | 100 |
|  |  | 0.5 months | 100 |
|  |  | 1 month | 100 |
|  |  | 2 months | 100 |

EXAMPLE 13

The formulations of the present invention have a good disintegration property. Accordingly, when the formulation is administered via the buccal cavity or oral route, it is disintegrated at a suitable rate to release the active component. Table 2 below shows the disintegration time and the density of the formulations which were prepared in Examples. Disintegration time was determined according to Disintegration Test (JP XII), by using water as a test liquid, adding the supplemental plates, and moving up and down at 37° C., to observe the disintegration time or dissolution of the formulations.

TABLE 2

| Example number | Conc. (%) of aqueous solution before drying | | Ratio (%) of COL. | Density | D.T. |
|---|---|---|---|---|---|
| | COL. | T.E | COL./T.E. | (mg/cm³) | (min.) |
| 1 | 1 | 8 | 25 | 80 | 5 |
| 2 | 1 | 8 | 25 | 80 | 5 |
| 3 | 1 | 8 | 25 | 80 | 5 |
| 4 | 1 | 5 | 20 | 50 | |
| 5 | 1 | 4 | 25 | 40 | |
| 6 | 1 | 4 | 25 | 40 | |
| 7 | 1 | 4 | 25 | 40 | |
| 8 | 2 | 6 | 33 | 60 | |
| 9 | 2 | 5 | 40 | 50 | |
| 10 | 1.5 | 7 | 21 | 500 | |
| 11 | 12 | 29 | 40 | 1000 | |

COL: collagen, T.E.: total excipient, D.T.: disintegration time.

REFERENCE 1

In vitro release behavior of the spongy formulation which was prepared in Example 2 was examined, and compared with the collagen needle pellet which was prepared according to the method described in Example 1 of the Japanese Patent Publication (kokai) No. 228028/1987.

The method of preparing the collagen needle pellet of the Japanese Patent Publication (kokai) No. 228028/1987 is provided blow.

Five ml of an aqueous solution containing the desalted interferon-α (20 millions IU/ml) was added to 2 g of atelocollagen, and the mixture was swelled in a refrigerator for 20 hours. To the mixture was added 1.6 ml of 1N hydrochloric acid and distilled water was added until the total weight reaches 10 g, and the mixture was fully stirred and dissolved in a mortar to give a homogeneous mixture. The mixture was placed into a 10 ml disposable syringe, and centrifuged at 10,000 G for 30 minutes so that the mixture was degassed. This mixture was pushed out from a nozzle having 2 mm i.d., which had been attached to the syringe, and the mixture was placed into a groove on an acryl plate in which a round groove is made in a linear condition, while the syringe was moved at the same speed as that of the exudation of collagen pushed out. This mixture was placed into a desiccator where the relative humidity was kept 65%, and dried for 24 hours. The resultant dried products were placed in an atmosphere of an ammonia gas to neutralize, and air-dried. Then, the dried product was cut into pieces having a suitable length, to yield homogeneous needle pellets having 1 mm±2% diameter, each of which contains 100,000 IU of interferon-α. Thus, the needle pellets are different from the formulation of the present invention in that the formers are prepared from a solution having higher concentration of the carrier, collagen.

Each of the formulations was added to 1.5 ml of a test solution (PBS buffer containing 0.5% human serum albumin, 0.01% sodium azide), and the mixture was stirred at room temperature. The time-course of the concentration of interferon-α in the mixture was determined by RIA.

Figure 2:
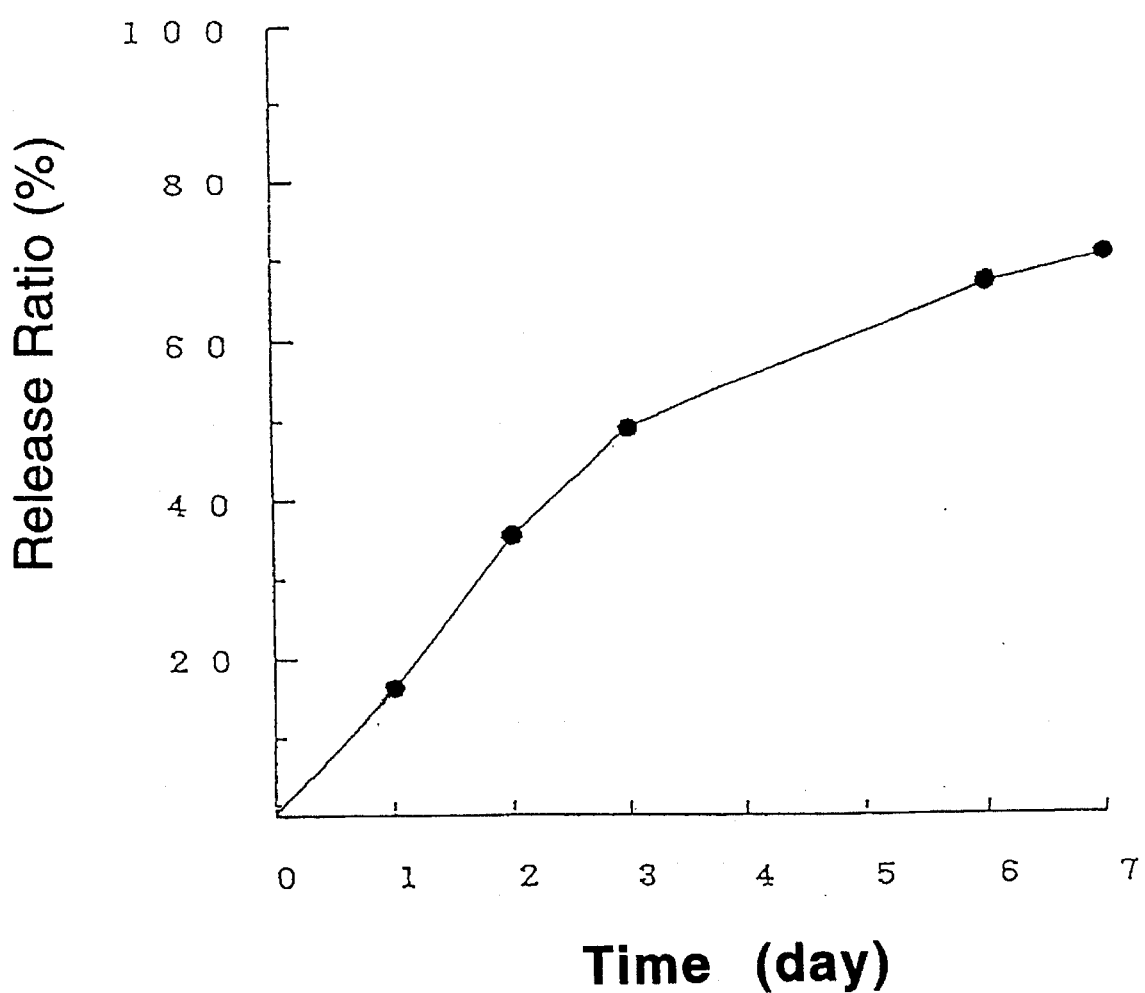
FIG. 2 shows a release of interferon from the collagen needle pellet as a control.

The results are shown in FIGS. 1 and 2. In the figures, the vertical axis shows the release ratio of interferon-α (unit: %), and the horizontal axis shows the time (unit: minutes or days). FIG. 1 shows the results of the spongy formulations of the present invention, and FIG. 2 shows the results of the collagen needle pellets of the reference.

From the data, it is obvious that the release rate of the active ingredient in the spongy formulation of the present invention is faster than that of the collagen needle pellet.

What is claimed is:

1. A spongy formulation for buccal or oral administration which contains a therapeutically effective amount of a proteinaceous physiologically active substance as an active ingredient, collagen and a water-soluble additive, said formulation being characterized by having a density of 10 mg/cm$^3$ to 500 mg/cm$^3$, a porosity of from 99% to 23% and a disintegration time of from 1 minute to 30 minutes.

2. The spongy formulation of claim 1, which is obtained by drying by in vacuo lyophilization.

3. The spongy formulation of claim 1, wherein the proteinaceous physiologically active substance is interferon.

4. The spongy formulation of claim 2, wherein the proteinaceous physiologically active substance is interferon.

5. The spongy formulation of claim 1, 2, 3 or 4, wherein the weight ratio between collagen and the water-soluble additive is 1:9 to 9:1.

6. The spongy formulation of claim 1, 2, 3, or 4, wherein the weight ratio between collagen and the water-soluble additive is 1:9 to 1:1.

7. A spongy formulation for treating AIDS, which is suitable for buccal or oral administration, and which contains a therapeutically effective amount of interferon as an active ingredient, collagen and a water-soluble additive, said formulation being characterized by having a density of 10 mg/cm$^3$ to 500 mg/cm$^3$, a porosity of from 99% to 23% and a disintegration time of from 1 minute to 30 minutes.

8. A spongy formulation for preventing the progress of AIDS, which is suitable for buccal or oral administration, and which contains a therapeutically effective amount of interferon as an active ingredient, collagen and a water-soluble additive, said formulation being characterized by having a density of 10 mg/cm$^3$ to 500 mg/cm$^3$, a porosity of from 99% to 23% and a disintegration time of from 1 minute to 30 minutes.

* * * * *